United States Patent [19]

Haimson

[11] 4,130,759
[45] Dec. 19, 1978

[54] METHOD AND APPARATUS INCORPORATING NO MOVING PARTS, FOR PRODUCING AND SELECTIVELY DIRECTING X-RAYS TO DIFFERENT POINTS ON AN OBJECT

[75] Inventor: Jacob Haimson, Mountain View, Calif.

[73] Assignee: Haimson Research Corporation, Palo Alto, Calif.

[21] Appl. No.: 778,615

[22] Filed: Mar. 17, 1977

[51] Int. Cl.² ............................................. G03B 41/16
[52] U.S. Cl. ............................... 250/445 T; 250/402; 313/55
[58] Field of Search ................... 250/445 T, 401, 402, 250/403, 419; 313/55, 57

[56] References Cited

U.S. PATENT DOCUMENTS

| | | | |
|---|---|---|---|
| 2,453,798 | 11/1948 | Kloos | 250/419 |
| 4,002,917 | 1/1977 | Mayo | 250/445 T |
| 4,031,395 | 6/1977 | Le May | 250/445 T |
| 4,045,672 | 8/1977 | Watanabe | 250/445 T |
| 4,048,503 | 9/1977 | Taylor | 250/445 T |

Primary Examiner—Craig E. Church
Attorney, Agent, or Firm—Limbach, Limbach & Sutton

[57] ABSTRACT

A method and apparatus for producing high intensity x-rays and directing such x-rays toward an object of interest from a fixed annular target by producing a high power electron beam, selectively directing that beam by means of selectively activating electromagnetic elements having no mechanically moving parts to preselected points on the target for production of x-rays therefrom and correcting selected beam aberrations imposed upon the electron beam by the beam directing elements.

65 Claims, 21 Drawing Figures

METHOD AND APPARATUS INCORPORATING NO MOVING PARTS, FOR PRODUCING AND SELECTIVELY DIRECTING X-RAYS TO DIFFERENT POINTS ON AN OBJECT

BACKGROUND OF THE INVENTION

This invention relates generally to apparatus and a method for generating and directing high intensity x-rays. More particularly, it relates to apparatus for producing and directing such high intensity x-rays to an object of interest from any of a plurality of preselected points spaced from that object. More specifically, the invention relates to such apparatus which is suitable for use in a computer tomography (CT) x-ray scanner having no moving parts.

Conventional high intensity x-ray scanning equipment, such as is used in conventional computer tomography scanners currently available, generally incorporate one or more x-ray sources and detectors which are mechanically rotated together about an axis generally extending horizontally through the apparatus and through the object of interest. However, since the x-ray producing and detecting apparatus which must be rotated is relatively large and heavy with the source and the detecting apparatus being spaced generally several feet apart, the accelerating, centrifugal, and braking forces which must be exerted to rotate and stop the apparatus for rapid and accurate repositioning at numerous points are necessarily great and apply large stresses to both the cathode and the target assemblies of the x-ray generating tube. Additionally, the commonly used rotating target assemblies further experience large gyroscopic forces. These forces produce design difficulties and service life limitations on the apparatus. Further problems associated with these mechanically moving systems arise from the motor drive equipment, moving interconnections, slip ring assemblies, and other mechanical elements, especially with the continuing demands for increasing scan speeds and higher beam powers. Thus, when seeking further performance improvements, the conventional mechanical drive systems which must be designed to move rapidly and to accurately position the x-ray tube and its associated apparatus present severe inertial limitations and require substantial performance compromises.

The obvious approach to take to obtain further performance improvements in scan speed while avoiding these inertial limitations is through the use of an electronically scanned system which has no moving parts to present such limitations. However, the physical properties of an electron beam suitable for the production of such x-rays, and the interaction of such a beam with the scanning elements present a number of nonobvious problems which heretofor have defied solution and have prevented the development of an operable no-moving-part x-ray scanner of sufficient power to be useful, especially for computer tomography applications. The primary problems encountered have been those imposed upon focal source geometry by the space charge forces of the electron beam used to produce the x-rays and the field aberrations introduced into the beam by the beam deflecting elements. The only prior art patent known to the inventor which suggests such an electronically scanned x-ray system, Oldendorf U.S. Pat. No. 3,106,640, fails completely to address these major problems and thus, despite its relatively low energy (30 kv) electron beam, is of questionable usefulness and operability as disclosed in that patent.

Consideration of the case of a high current, high voltage x-ray scanner, such as might be used for computer tomography and which incorporates an annular or ring target with an electron beam deflected to that target from an initial trajectory along the axis of the ring, is useful for illustrating the problems necessary for solution to obtain an operable electronically scanned x-ray system. For such a case a straightforward analysis of the forces acting upon the electron beam shows that, for the required practical values of beam power, drift distance and x-ray focal source dimensions, the concept of simply deflecting the electron beam onto a large diameter ring target is not feasible for several fundamental reasons, one of the most important being the spreading of the beam due to space charge defocussing forces.

An initially parallel beam of electrons will, in free space, become increasingly divergent due to the presence of the inherent space charge of the electrons. The magnitude of these beam-spreading space charge forces at any point along the beam trajectory is a function of the electron beam energy, current and geometry. Neglecting the presence of ions, for a steady flow of electronic charge of constant density (as may be obtained with a direct current electron beam drifting in free space) the distance (z) that an initially parallel beam of radius $r_0$ can drift before space charge forces have caused the beam to diverge to a larger radius r is given by the following relativistically corrected universal beam spreading formula:

$$z = r_0/\sqrt{i}(\gamma^2-1)^{\frac{1}{2}} G \text{ in MKS units.}$$

where i = electron beam current in amperes
$\gamma$ = energy of the electrons in rest mass units
and $$G = \left[\frac{m_o}{e} 4\pi \epsilon_o c^3\right]^{\frac{1}{2}} \int_0^x e^{x^2} dx$$

where $m_o/e$ = ratio of the electron rest mass to charge
$\epsilon_o$ = permittivity of free space
c = velocity of light
and $x = (\ln r/r_0)^{\frac{1}{2}}$ — a factor representing the geometric expansion of the beam.

The space charge modified behavior of the more practically encountered non-uniform charge density beams require rigorous three dimensional analyses of the variations of charge density, beam energy and beam geometry with distance traveled. The beam core potential depression and reduced space charge effects due to the presence of surrounding walls also have to be taken into account. Such analysis may be found in Haimson and Mecklenburg, *A Relativistically Corrected Three Dimensional Space Charge Analysis of Electron Bunching,* IEEE Transactions on Nuclear Science, June 1967, pp. 586-93. However, for purposes of illustration, the simplified equation given above may be used with following desirable parameters for an advanced, electronically scanned x-ray CT scanner:

beam energy — 130 kilovolts (kv);
beam currents — 250 to 500 mA;
drift distance from beam deflector to x-ray ring target — 2 to 2.5 meters.

This drift distance is chosen to provide a vacuum chamber suitably large to comfortably encompass a patient undergoing computer tomography and to ensure sufficient traversal of the patient's longitudinal axis to permit a whole body scan procedure. By utilizing these parameters the above-described analysis requires that, to achieve an x-ray focal source diameter of 1 mm, the initial beam diameter must be larger than that by a factor of 100. Such adverse beam geometry would require a large and cumbersome drift space housing and special electron beam and gun optics and would substantially aggravate the beam aberration effects imposed upon the beam by the deflecting elements. These aberration effects also impose fundamental restrictions on achieving a narrow focal source on a large diameter ring target when using a simple deflection system (such as disclosed by Oldendorf) and a high current electron beam, as is required for computer tomography applications. Such a simple deflection system as disclosed in Oldendorf also requires the use of an undesirably large and long drift space housing due to its conical beam path between the deflection coil and the target.

To overcome the space charge limitations upon the system, conventional practice in the design of other types of electron beam devices has been to provide a simple axial magnetic field to enable the beam cross-section to be controlled by compensating for the divergence caused by the space charge forces. However, the use of such conventional extended solenoid coils located outside the vacuum chamber would be most undesirable in a high intensity computer tomography scanner for several reasons. Not only would the partial compensation of the deflection forces have to be accounted for, but, more importantly from the x-ray production and detection point of view, the electron beam so controlled would strike the target with very large azimuthal velocity components (in a direction circumferential to the ring target). For systems which incorporate radially oriented x-ray collimators in order to improve detection and to minimize oblique absorption and penumbral contribution to the patient's total integrated dose of radiation, these problems result in a substantial loss of x-ray intensity for a given electron beam energy.

Another serious limitation encountered by the use of a simple deflection system to deflect a high current electron beam onto a large diameter annular target is that the minimum size and desired shape of the focal source on the target are strongly influenced by aberrations introduced by the beam deflection system and by any other electromagnetic field elements located between the deflection system and the electron beam source. Very small initially introduced beam aberrations are highly amplified due to the long drift distance and large deflection which is necessary for such a CT system. Even if the effects of space charge beam spreading and finite emittance of the beam source are neglected, the requirement to reproduce a given focal source geometry to within, for example, 1 mm at the target, demands both an extremely high quality characteristic of the beam entering the deflector and an extremely high quality, homogeneous deflection field which is free of higher order aberrations, regardless of the size of the beam and the varying position of the beam in the field during traversal of the deflector.

Even if these various aberration effects could be individually neutralized for a given position on the target, (i.e., a specific deflection field configuration) the other azimuthal locations of the focal source, which require different deflection field configurations, would interact with the imperfect entry beam in a non-linear fashion to produce space- and time-dependent aberrations at the focal source. The degree of difficulty in overcoming these focal source distortions is increased even further by the need for designing an x-ray scanner for a CT system in which the electron beam can be switched rapidly, in microseconds, not just from one focal source position to the next contiguous location on the target, a few millimeters away, but to another focal source position that may be almost diametrically opposite and then back across to the opposite side of the patient again. In such a system, the detectors must also be gated in synchronism with the fast switching electron beam locations.

SUMMARY OF THE INVENTION

In view of the foregoing requirements it is an object of the present invention to provide a high power x-ray scanning apparatus having no moving parts. It is a further object of the invention to have such an apparatus which is designed specifically to minimize the restrictions imposed upon focal source geometry by space charge forces and field aberrations. It is a further object of the invention to provide such an apparatus which enables a high power electron beam to be deflected over long distances and directed onto a target circumscribing the axis of an object of interest. It is yet another object of the invention to provide such an apparatus which has a narrow focal source and allows a plurality of x-ray beams to be directed generally radially inward from a series of predetermined azimuthal positions around the periphery of such an annular taret. Other objects of the invention are to provide such apparatus in which the electron beam may be made incident upon the target at an angle favorable to the production of x-rays and which may provide a large diameter internal cavity for receiving an object to be scanned while limiting the outside dimensions of the apparatus. It is yet a further object of this invention to provide a method of producing and directing such x-rays with nonmechanical scanning.

To achieve the above objects and others, apparatus is disclosed for producing high intensity x-rays and directing such x-rays toward an object of interest from any of a plurality of preselected coplanar points spaced from that object and spaced radially about a line extending through that object. The apparatus disclosed has no moving parts and includes means for producing a high voltage, high current electron beam and stationary target means encompassing the coplanar points for receiving the electron beam and producing x-rays therefrom and directing them toward the object of interest. An evacuated housing contains the beam producing means adjacent one end and the target means adjacent the other end. The apparatus further includes means for directing the electron beam selectively to preselected points from the target and beam shaping means for shaping the beam to a predetermined cross-sectional configuration at its point of incidence on the target and for correcting beam aberrations introduced by the beam directing means. Additionally, a method is described for producing and directing high intensity x-rays toward the object of interest from such target with a combination of the beam directing means and beam shaping means compensating for the effect of space charge forces acting on the beam and correcting the field aberrations imposed thereupon.

BRIEF DESCRIPTION OF THE DRAWINGS

FIG. 1a is a fragmentary side sectional view of a variaion of the apparatus of FIG. 1 with a beam collector mounted off the longitudinal axis;

DESCRIPTION OF A PREFERRED EMBODIMENT

Figure 1:
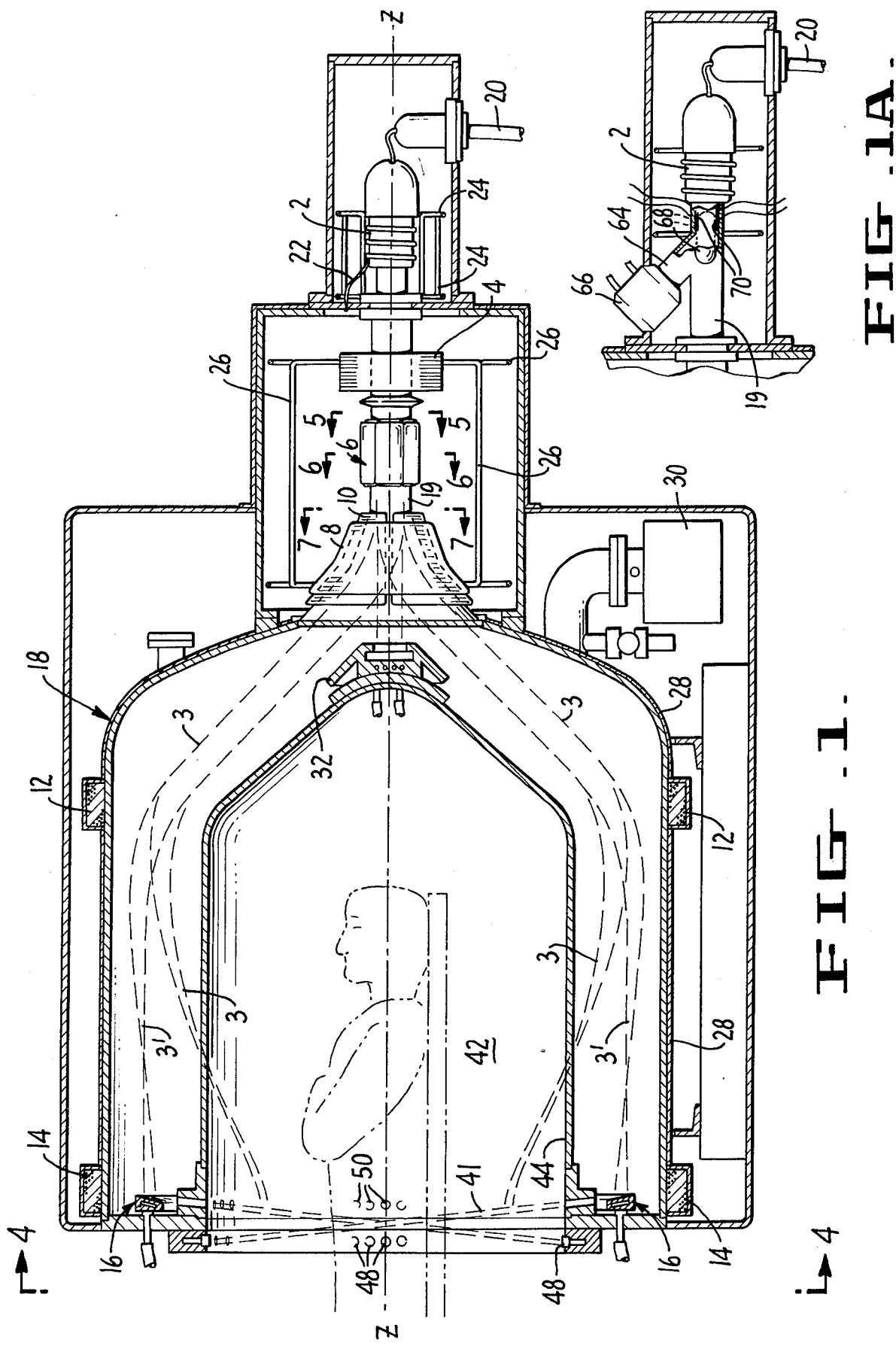
FIG. 1 is a side sectional view of the x-ray producing and directing apparatus of this invention.
Figure 2:
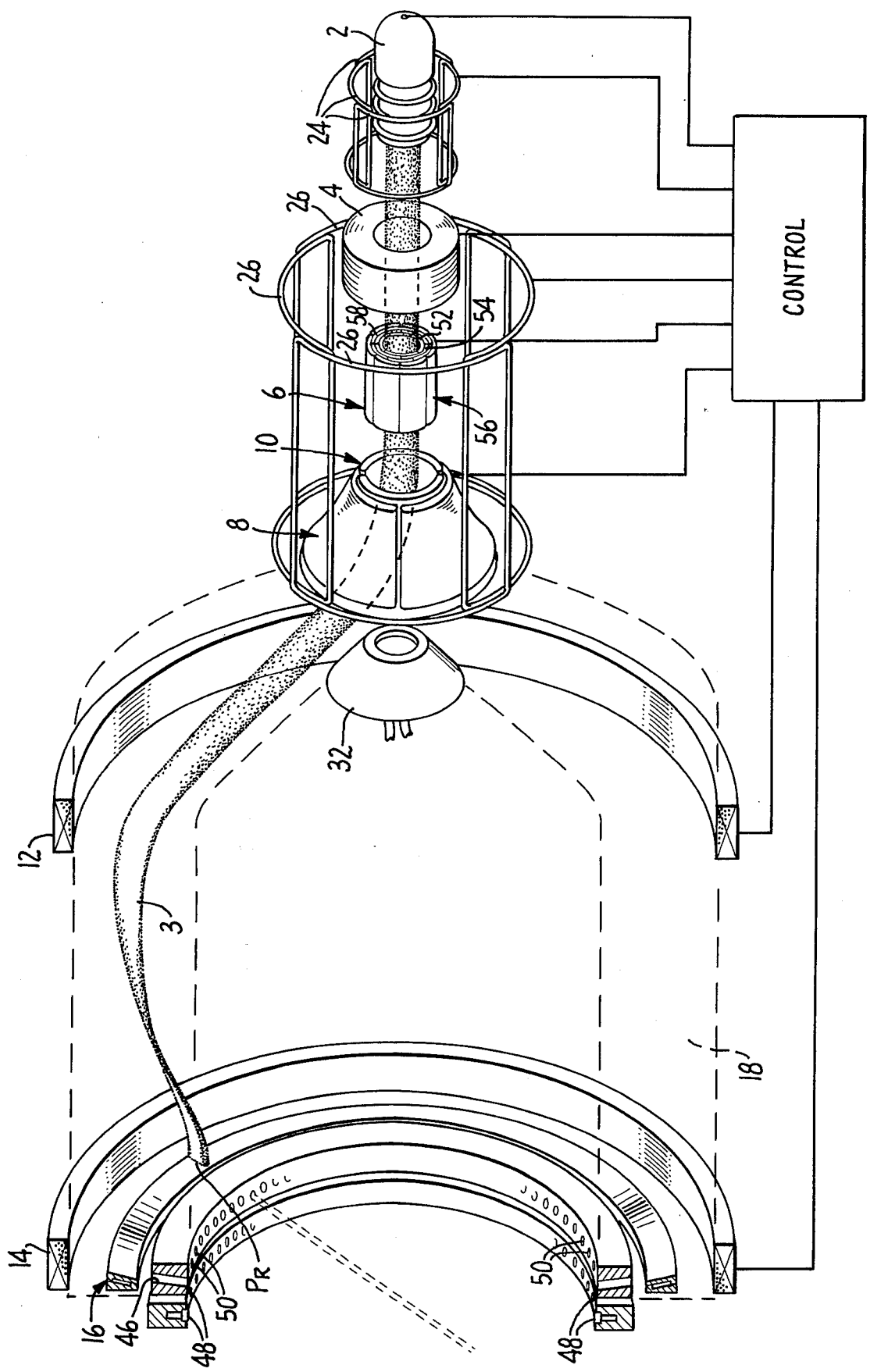
FIG. 2 is a schematic, perspective plan view of the basic elements of the apparatus of FIG. 1, illustrating the trajectory of an electron beam therethrough.

One preferred embodiment of the x-ray producing and directing apparatus of this invention is illustrated in the side sectional view of FIG. 1, with its principal active components illustrated in the schematic perspective plan view of FIG. 2. In this embodiment of the invention the basic components comprise an electron gun 2 for producing a high voltage, high current electron beam 3, an electromagnetic preliminary focussing coil 4, a multipole winding assembly 6 for shaping the beam and correcting for aberrations therein, a pair of electromagnetic field dipole assemblies 8 and 10 for deflecting the electron beam off the longitudinal axis, a pair of electromagnetic focussing coils 12 and 14 for focussing the electron beam, target 16 for receiving the electron beam and producing x-rays therefrom, and an evacuated housing 18 containing the foregoing elements with the electron gun adjacent one end and the target adjacent the opposite end. As illustrated, the electron gun is generally aligned along the longitudinal axis of the apparatus, Z—Z, which is illustrated in this embodiment as being substantially horizontal. In this embodiment the beam deflecting dipole assemblies 8 and 10 along with the focussing coils 12 and 14 generally comprise the electron beam directing means, and the preliminary focussing coil 4 and multipole winding assembly 6, described more specifically below, comprise the beam shaping means.

Figure 3:
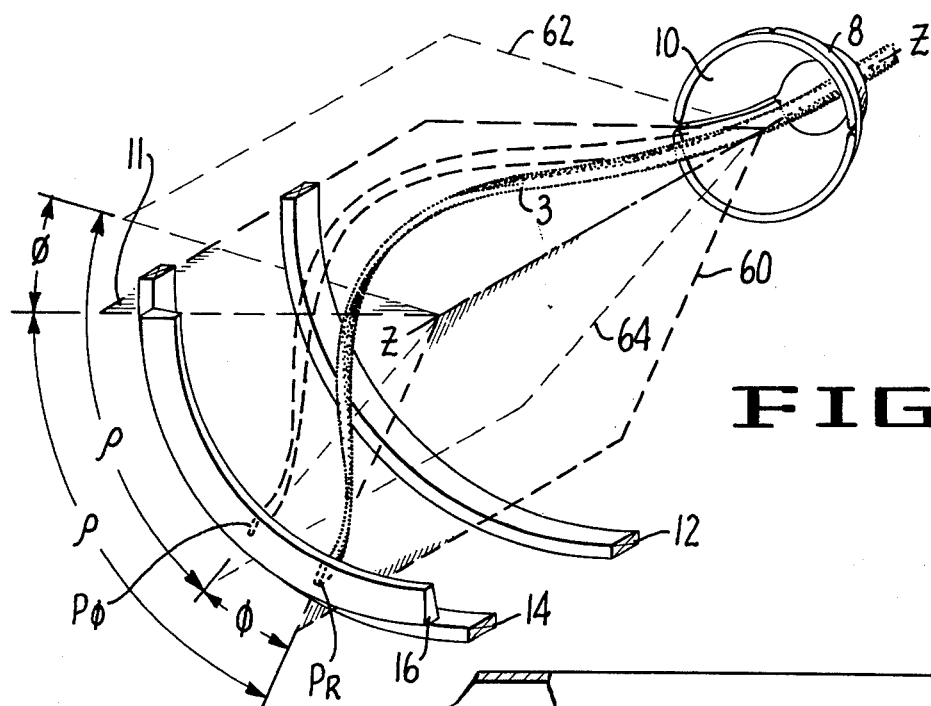
FIG. 3 is a schematic front perspective view illustrating the path of the beam of FIG. 2 between the dipole assemblies and the target.

The general manner of operation of this apparatus is basically as follows: the electron beam 3 is produced by the low emittance, long focal length, high voltage electron gun 2, passes through the preliminary focussing coil assembly 4 and multipole winding assembly 6. The beam 3 then enters the deflection system comprising the dipoles 8 and 10, which impart a relatively high radial momentum to the beam and cause it to be deflected from the axis Z—Z as it enters the large annular vacuum chamber 18, shown in FIG. 1. As the deflected electron beam 3 approaches the outer wall of the chamber 18, it enters the weak focussing field of the large diameter electromagnetic coil 12, to which a direct current is applied to create an electromagnetic field. The radial and axial electromagnetic field components of this electrically charged coil 12 interact respectively with the axial and radial velocity components of the electron beam to impart an azimuthal, or circular, velocity to the beam, thus causing the beam to rotate about the axis Z—Z, as shown in FIGS. 2 and 3. This azimuthal motion of the beam interacts with the coil 12 axial field components to produce forces which both provide focussing, due to the field gradient acting on different portions of the beam with differing force, and counteract the radial velocity imparted by the dipole assemblies 8 and 10. Suitable adjustment of the DC current level in the coil 12 enables the radial velocity of the beam to be reduced to a very low value when passing through this field. Thus, the beam continues to drift through the field of the coil 12 with essentially axial and azimuthal velocity components until it enters the weak focussing field of the second large diameter focussing coil 14. This second focussing coil 14 is energized with a direct current having a polarity in opposition to that of the coil 12. Additionally, the magnitude of the electromagnetic field of coil 12 preferably is adjusted such that the net axial electromagnetic field component acting upon the electron beam is reduced to about zero at the plane of the target 16, which is illustrated as being in close proximity to coil 12 in FIG. 1. By arranging for the axial component of the electromagnetic field to be reduced to zero in this manner, the azimuthal beam velocity components introduced by each of the opposing lenses 12 and 14 cancel one another so that the net azimuthal velocity of the electron beam is reduced substantially to zero as it strikes the incident surface of the x-ray target 16.

Figure 8:
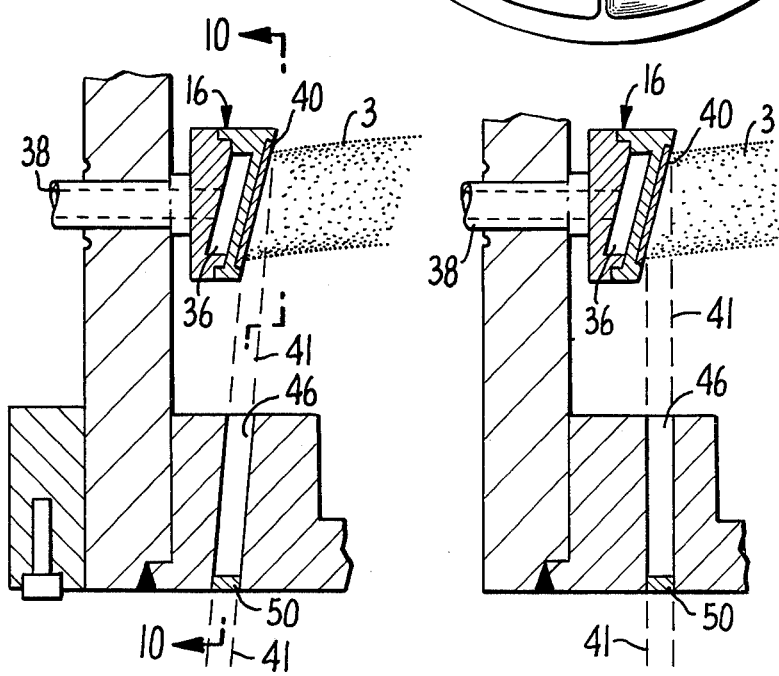
FIG. 8 is a sectional view, at an enlarged scale, of the target and collimating structure of the apparatus of FIG. 4, taken along line 8—8.
Figure 9:
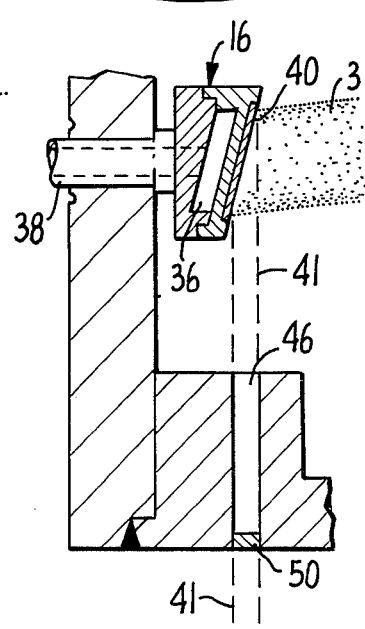
FIG. 9 is a sectional view of a variation of the apparatus of FIG. 8.
Figure 10:
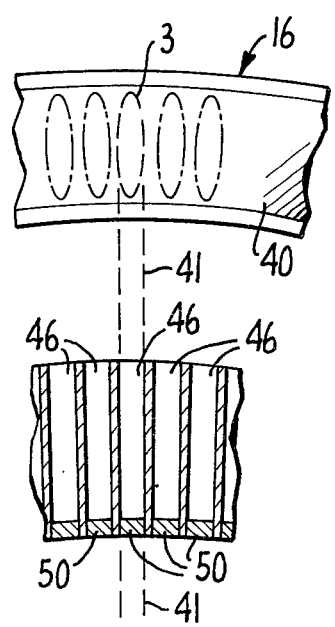
FIG. 10 is a sectional view of the apparatus of FIG. 8, taken along line 10—10.

It may be noted that in traversing the second focussing coil 14, in which the direction of both the azimuthal acceleration and the actual magnetic field are reversed with respect to that of coil 12, the beam 3 continues to experience a net focussing force due to the field gradient of that coil. Thus, the beam 3 is subject to a continual focussing force from the beginning of its trajectory upon entering the electromagnetic field of coil 12 until it strikes the x-ray target 16 located adjacent the end of the vacuum chamber 18. By suitable choice of the number of turns in each focussing coil 12 and 14, and by locating these shielded coil assemblies at their optimum locations, it is possible to use a single constant current power supply to energize both focussing coil assemblies 12 and 14 to provide for simple operation over a range of different electron beam energies. Thus, the combined action of the two large diameter, opposing field electromagnetic focussing coils 12 and 14 thereby provide not only a means of eliminating the undesirable azimuthal velocity component of the beam at the target plane, but also a means of controlling beam spreading due to the space charge forces. This is of substantial advantage in such an x-ray scanning system, since studies have shown that the use of conventional solenoidal focussing causes the electrons to be incident on the annular target with large components of azimuthal velocity. Such azimuthal velocity results in a loss of x-ray intensity when using radial collimation on the x-rays directed toward a patient. Additionally, a highly stable azimuthal position of a point focal source, or a radially oriented line source, as illustrated in FIGS. 8, 9 and 10, on the target becomes much more difficult to achieve with azimuthal velocity at the target. Such a radially oriented line focal source has definite system advantages in that it serves to reduce the power density per unit area at the target 16, while maintaining a high average power on the target for production of x-rays, and it provides a powerful means of extending the space charge spreading current limitations of a circular cross-section beam. Also, such a radially oriented line source enables the size of the x-ray primary collimator and the projected x-ray beam in the direction parallel to the longitudinal axis Z—Z of the system to be predetermined and quite small by suitable selection of the angle between the target 16 incident surface 40 and the electron beam, as illustrated in FIGS. 8, 9 and 10.

The electron gun 2 is preferably one having low emittance characteristics, such as described by this inventor in *Recent Advances in High Voltage Electron Beam Injectors*, IEEE Transactions on Nuclear Science, NS-22, June 1975, pages 1354–57. Current is provided to this electron gun from a suitable high voltage power source (not shown) at the opposite end of cable 20. As described in the above reference paper, a fiber optics light link 22 may suitably be provided for pulsing the electron gun, in a manner to be described below.

Vacuum chamber 18, which is generally bell-shaped with internal and external walls defining the evacuated chamber, also includes an elongated generally cylindrical neck portion 19 extending between the dipole assemblies 8 and 10 and the gun 2. The bell portion of the vacuum chamber is preferably formed of a non-magnetic material such as stainless steel, with the neck 19 being formed of a suitable dielectric material, such as glass. The electron gun 2 and the drift space between the electron gun and the dipole assemblies 8 and 10 are provided with Helmholtz compensating coils 24 and 26, and the bell-shaped housing 18 is provided with magnetic shielding 28 to avoid undesirable beam steering effects due to local magnetic anomalies and the earth's stray magnetic field. A suitable vacuum pump 30 is mounted in communication with the interior of the vacuum chamber 18 to maintain the desired vacuum.

Target 16, shown more clearly in the fragmentary sectional views of FIGS. 8, 9 and 10, is positioned within the vacuum chamber adjacent the outer end of that horizontal, bell-shaped chamber 18 and encompasses the coplanar points from which x-rays are to be directed at the patient or other object of interest. Preferably, this target is a continuous ring-like annular member having an interior chamber 36 connected to an inlet 38 and an outlet (not shown) for passage of a cooling fluid, such as water, therethrough, to remove the heat generated by the impingement of the electron beam upon the target. Preferably, the target assembly 16 is formed primarily of copper to facilitate the transfer of heat to such cooling fluid. By the use of this relatively large area, continuous, fixed target, the average power density of the electron beam on the target is relatively low despite the high intensity of the beam at its point of impingement, thus avoiding the difficulties presently encountered with increased beam power in conventional rotating target x-ray tubes. On the portion of the target facing the impinging electron beam 3, which is indicated by the generally horizontal broken lines in FIGS. 8 and 9, is a target inlay 40, preferably of tungsten, for receiving the electron beam 3 and producing the desired x-rays 41 (the broken line beam extending generally downwardly in FIGS. 8, 9 and 10) therefrom.

FIG. 8 represents a fragment of the target assembly illustrated in FIGS. 1 and 2, in which the angle between the incoming electron beam 3 and the tungsten target inlay 40 is set to direct the x-rays toward the axis Z—Z slightly longitudinally outwardly of the cavity 42 defined by the inner wall 44 of the vacuum housing 18. Collimating elements, in the form of apertures 46 in a ring radially inward of the target 16, are aligned with the x-ray beam emerging from the target inlay 40. These collimating apertures 46 are further aligned with x-ray detectors 48, which are positioned across the cavity 42, and serve to eliminate stray radiation which might otherwise reach undesired portions of the patient, and also to reduce crosstalk between different portions of the target and their respectively opposed detectors. A suitable x-ray-transmissive window 50 covers and seals the radially inner end of each collimating element 46 to maintain the integrity of the vacuum chamber 18. FIG. 10, the sectional view taken along line 10—10 of FIG. 8, illustrates the projected image 52, which is a very narrow, generally elliptical shape approaching a line projection, of the electron beam on the angled target inlay 40 such that the projected x-ray beam may be round or slightly oval in cross-section as it comes off the target inlay 40.

FIG. 9 illustrates a minor modification to the target structure described above, in which the target 16 is angled such that the x-ray beam is directed radially inwardly normal to the longitudinal axis Z—Z of the apparatus of FIG. 1. With such an arrangement it would be necessary to interpose the individual detector elements between adjacent collimating elements 46 to receive the x-ray beam from the diametrically opposed target portion. Such an arrangement tends to render this alternative structure slightly more difficult to manufacture than that of FIG. 8. Of course, it is also apparent that, in the place of continuous ring target assembly 16, a plurality of discrete target elements encompassing the same coplanar points of impingement of electron beam, spaced radially about the axis Z—Z, could be substituted with equal operability, although the ease of manufacture and cooling of such structure may be substantially compromised with respect to that preferred structure described above.

FIG. 2 provides a top or plan perspective view, partially in section, of the principal active elements of the apparatus of this invention, all of which have been briefly described above. The shaded beam 3 extending from one end of the electron gun 2 to the target 16 represents the electron beam of this apparatus being directed to one of the preselected points about the target from which x-rays are desired to be produced. For clarity the vacuum chamber 18 and its neck 19 have been omitted from this view, with their general outlines only illustrated in phantom. This beam position is exactly the same as is illustrated in the partial front perspective view of FIG. 3 and as illustrated by the heavy broken line in FIG. 4. These illustration are useful in illustrating the apparatus used for directing and shaping the electron beam and for correcting aberrations introduced by the various active elements and compensating for the effect of space charge.

The basic elements used for deflecting the beam are the two electromagnetic field dipole assemblies 8 and 10. While either the electric field or magnetic field dipoles could be employed for this purpose, the preferred embodiment is illustrated with magnetic field dipoles in the form of electrically energized coil assemblies. These electromagnetic dipole assemblies 8 and 10 are arranged such that their poles are oriented orthogonally with respect to one another and with respect to the direction of the electron beam, so that by independently controlling the strength of each dipole field the beam can be deflected in any desired direction from the axis Z—Z. In this embodiment the first dipole assembly 8 is oriented about the axis Z—Z such that it has a pole lying in a horizontally extending plane, which is defined as the dipole reference plane 11 in FIG. 3.

While a magnetic dipole can readily be obtained by locating two uniformly wound coils on diametrically opposite sides of the beam, the investigation of the beam after it has been deflected by such a dipole field will reveal distinct distortions of the beam cross-section due to the presence of higher order field modes or inhomogeneities. The severity of these beam distortions depends upon a variety of factors, the most important of which are the geometry of the various coil windings, the angle of deflection and the drift distance from the exit plane of the dipole to the plane of the application of the beam (the target). The two most dominant field aberrations that can be expected after interaction with a strong dipole field are those due to the quadrupole and sextupole higher order fields.

Theoretical analyses, such as found in W. R. Smythe, *Static and Dynamic Electricity*, (New York: McGraw-Hill, 1950), p. 279, on means of producing homogeneous field distributions for multi-mode magnets formed around a cylinder and having windings which are approximately parallel to the axis of the cylinder indicate that electrical current sheets of small radial thickness should be formed on the cylindrical surface according to the function $I_\sigma = I_o \cos(n\sigma/2)$ where $I_\sigma$ is the current surface density, n is the number of poles and $\sigma$ is the angular position of any portion of the coil from an antipole. In the preferred embodiment the beam directing dipole comprises two such cosine current distribution dipole assemblies 8 and 10, having poles which are orthogonal to one another as well as to the beam axis Z—Z. With this arrangement the electron beam can be deflected rapidly to any azimuthal location on the target 16 by applying the appropriate positive or negative ratio of drive currents, described below, to each of the two magnetic dipole assemblies 8 and 10. It may be noted that, for a given beam energy and current, the location of and the current applied to the large diameter coils 12 and 14 remain constant. It may also be noted that, by energizing each dipole assembly with drive currents having sinusoidally time-dependent amplitudes phased in quadrature, the electron beam will be deflected in such a manner as to be caused to rotate around the target at an angular frequency ($\omega = 2\pi f$) where f is the periodicity of the dipole deflector drive currents.

From the foregoing it may thus be seen that the dipole assemblies 8 and 10 each are formed from a pair of electromagnetic dipole coils 8a, 8b and 10a, 10b, respectively. These coils are formed around the surface of rotation which comprises the flared neck of the vacuum chamber 18 where it joins the generally cylindrical neck 19. The windings of each of these coils are approximately parallel to the beam path along the axis Z—Z and are formed according to the above function such that the current surface density of each portion of each of the dipole coils is proportional to the cosine of the angle, taken about the longitudinal axis Z—Z, between such coil portion and an antipole of the coil. These coils then make up the dipole assemblies 8 and 10 which are the primary deflecting elements (functioning in combination with coils 12 and 14) for directing the electron beam 3 to various point on target 16.

Even with extreme care in the design and manufacture of the special current distribution dipole assemblies 8 and 10, residual aberrations of an unacceptable magnitude may still be present due to fringe field effects and imperfections, such as asymmetric charge distributions, of the beam entering the dipole assemblies. To provide a flexible means of compensating for these undesirable residual effects, as well as a means of independently adjusting the cross-sectional configuration and orientation of the focal source at any azimuthal position on the target 16, a multipole winding assembly 6 is used in conjunction with the preliminary focusing coil 4. This assembly 6, which can be located on either side of the coil 4 but is shown between that coil 4 and the dipole assemblies 8 and 10, comprises two electromagnetic quadrupole assemblies 52 and 54 and two electromagnetic sextupole assemblies 56 and 58 formed around the neck 19 of the vacuum chamber as illustrated in FIGS. 1 and 2 and in the sectional views of FIGS. 5 and 6.

Figure 5:
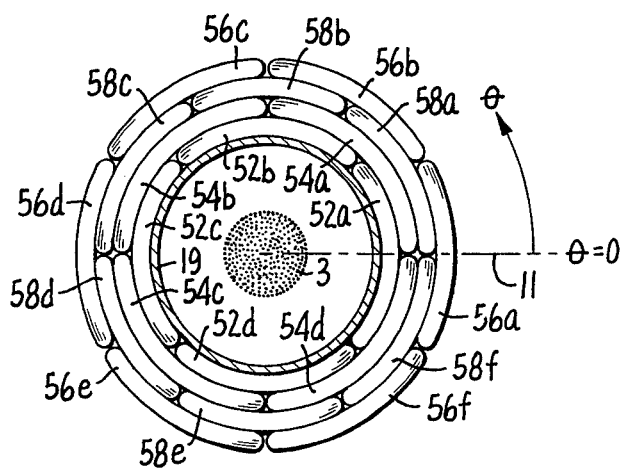
FIG. 5 is a sectional view illustrting the multipole winding assembly of the apparatus of FIG. 1, taken along line 5—5.
Figure 6:
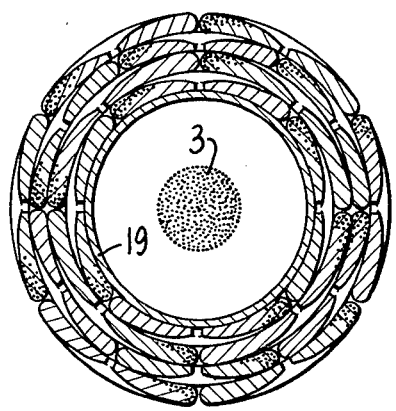
FIG. 6 is a sectional view of the multipole winding assembly of the apparatus of FIG. 1, taken along line 6—6.
Figure 7:
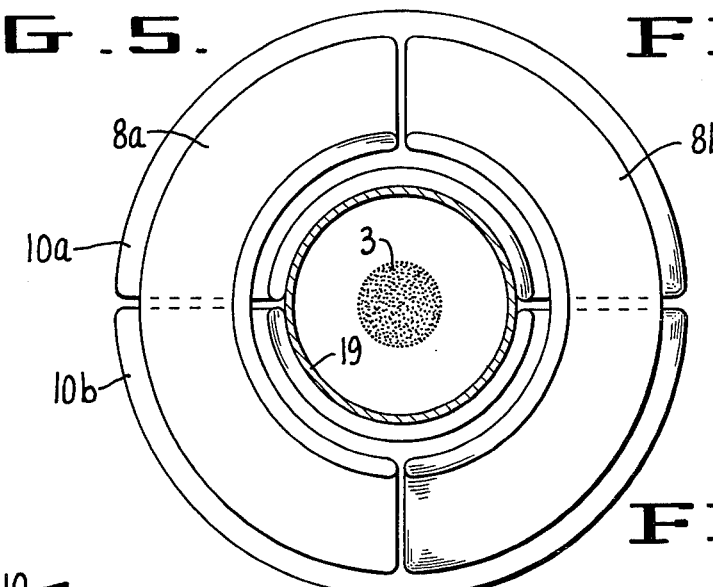
FIG. 7 is a sectional view illustrating the dipole assemblies of the apparatus of FIG. 1, taken along line 7—7.

The two quadrupole assemblies 52 and 54 are preferably formed of four electromagnetic coils each, 52a, 52b, 52c, 52d, and 54a, 54b, 54c, and 54d, respectively, which are formed about a surface of rotation, preferably the neck 19 of the vacuum chamber surrounding the beam path. Each of these coils has windings which extend approximately parallel to the beam path and, as illustrated in FIGS. 5 and 6, subtend sequentially adjacent arcs of approximately equal magnitude and thus of approximately 90° about the neck 19 of the chamber. Each of the coil windings 52a–d and 54a–d are formed in a manner well known to those skilled in coil design such that the current surface density of each portion of each coil is proportional to the cosine of the angle between such coil portion and an antipole of the coil. As illustrated in FIGS. 5 and 6 the first quadrupole assembly 52 is oriented about the longitudinal axis of the apparatus such that one pole of this quadrupole assembly 52 lies in the generally horizontal plane previously defined as the dipole reference plane 11. The second quadrupole assembly 54, also as illustrated in FIGS. 5 and 6, is concentric with the first quadrupole assembly 52 and is angularly displaced 45° about the longitudinal axis Z—Z with respect to the first quadrupole assembly 52. The cosine function desired of the current surface density when the current is applied to the quadrupole coils is obtained by jig winding the coils in a manner known to skilled coil designers such that each coil has very few layers of windings near the center of the coil with increasing numbers and thus thickness of windings outwardly of the center of the coil, as illustrated in the sectional view of FIG. 6, thus effecting the desired cosine function design.

The sextupole aberration correcting electromagnetic coil assemblies 56 and 58 are also illustrated in FIGS. 5 and 6. Each of these electromagnetic sextupole coil assemblies preferably is formed from six electromagnetic coils formed about a surface of rotation, preferably on the neck 19 of the vacuum chamber, and preferably concentrically overlying the quadrupole assemblies. Each of the six coils 56a-f and 58a-f have windings extending approximately parallel to the beam and beam path 3 along the horizontal axis and subtend sequentially adjacent arcs which are approximately equal in size and thus comprise approximately 60° about the vacuum chamber housing neck. Each of these coil windings 56a-f and 58a-f is also wound in the general configuration described with respect to the quadrupole coils, such that the current surface density of a current passing through the coil is proportional in each portion of the coil to the cosine of the angle between such coil portion and an antipole of the sextupole coil. As illustrated most clearly in FIG. 6, the first sextupole coil assembly 56 is oriented about the apparatus longitudinal axis such that one pole of this first sextupole coil assembly lies generally in the same horizontal plane which was previously defined as being the dipole reference plane 11. The second sextupole coil assembly 58 is preferably concentric with the first sextupole coil assembly 56 and is angularly displaced by an angle λ equal to 30° about the longitudinal axis with respect to the first sextupole coil assembly.

To explain the function of the multipole winding assembly 6, which comprises the various quadrupole and sextupole coil assemblies, reference is made to Table 1 below and the respective FIGS. 11a-11e and FIGS. 12a-12e, which illustrate the effects of various combinations of quadrupole and sextupole fields on the cross-section of the projected electron beam 3, disregarding the influences of the dipole assemblies 8 and 10 and the coils 12 and 14 for the moment for simplicity of explanation. The FIGS. 11a-11e and 12a-12e illustrate the effects upon beam shapes and beam orientation of the indicated electromagnetic fields produced by quadrupole assemblies 52 and 54 and sextupole assemblies 56 and 58 when the specified electromagnetic field amplitude and phases are produced in each of those assemblies by the application of predetermined electrical current to those assemblies, as will be described in more detail below.

Figure 11A:
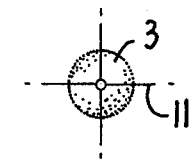
FIGS. 11a–11e illustrate the effects upon the electron beam cross-section shape and orientation from the quadrupole assemblies of FIG. 1.
Figure 11B:
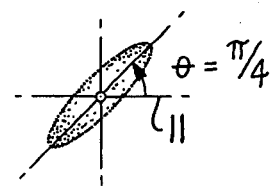
Figure 11C:
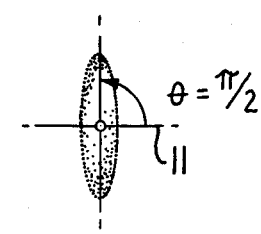
Figure 11D:
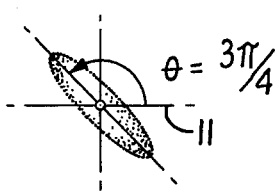
Figure 11E:
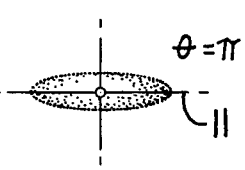
Figure 12A:
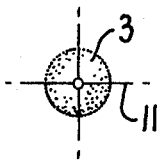
FIGS. 12a–12e illustrate the effects upon the electron beam cross-section shape and orientation from the sextupole assemblies of FIG. 1.
Figure 12B:
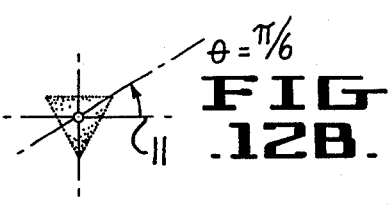
Figure 12C:
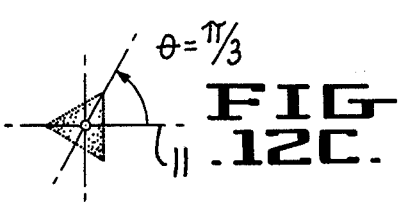
Figure 12D:
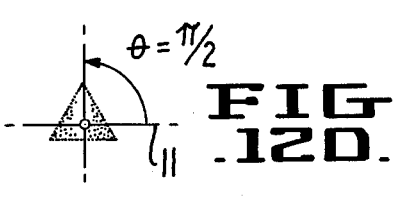
Figure 12E:
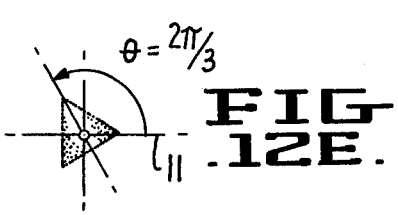

| Field Amplitude and Phase | | Electron Beam Cross-Section Shape and Orientation |
|---|---|---|
| Quadrupole 52 | Quadrupole 54 | |
| Zero | Zero | Fig. 11a |
| +Max, (π/2) | Zero | Fig. 11b |
| Zero, (π) | +Max, (π/2) | Fig. 11c |
| −Max, (3π/2) | Zero, (π) | Fig. 11d |
| Zero, (2π) | −Max, (3π/2) | Fig. 11e |
| Sextupole 56 | Sextupole 58 | |
| Zero | Zero | Fig. 12a |
| +Max, (π/2) | Zero | Fig. 12b |
| Zero, (π) | +Max, (π/2) | Fig. 12c |
| −Max, (3π/2) | Zero | Fig. 12d |
| Zero, (2π) | −Max, (3π/2) | Fig. 12e |

From the table and the FIGS. 11 and 12, it may be seen that, with the second quadrupole 54 de-energized (zero field amplitude), as the field strength of the first quadrupole 52 is increased from zero to a given positive maximum value, an initially circular cross-section beam will be transformed into a generally elliptical cross-section with the major axis oriented at an angle θ = 45° to a horizontal datum, suitably the horizontal plane defined as the dipole reference plane 11, as illustrated in FIG. 11b. The ratio of the major axis to the minor axis of this elliptical shape is a function of the power of the quadrupole assembly, the energy and diameter of the beam at entry to the quadrupole assemblies as determined by the preliminary focussing coil 4, and the subsequent action of the beam-spreading space charge forces. Reversal of the first quadrupole assembly 52 field, by passing it through zero and then to a given negative maximum value, will cause the beam cross-section to transform back to a circle and then to an elliptical shape again, with the major axis now oriented at 135° to the datum, the dipole reference plane 11, as illustrated in FIG. 11d. Thus, there is a change of π/2 in the spatial orientation of the focal source produced by a change of π in the quadrupole field direction. The second quadrupole assembly 54 electromagnetic fields will cause the beam focal source to exhibit similar characteristics, but with the pattern displaced in azimuth 45° with respect to the pattern produced by first quadrupole 52, due to the 45° angular displacement in the two quadrupole assembly windings.

In a manner similar to that described with respect to the quadrupole assemblies, when the sextupole assembly 58 is de-energized, increasing the field of the sextupole assembly 56 from zero to a given positive maximum value will tend to transform an initially circular cross-section beam (FIG. 12a) into one having a cross-section which approximates an equilateral triangle oriented such that a line through the center and one apex of the triangle is approximately 30° above the datum, the dipole reference plane 11, as illustrated in FIG. 12b. When the sextupole fields are reversed, going from a positive maximum value to a negative maximum value, the spatial orientation of the triangularly transformed beam cross-section will change by 60°, as illustrated by the difference in orientation between FIGS. 12b and 12d. The beam cross-section patterns produced by variation of the fields of the individual sextupole coils 56 and 58 will be generally identical but displaced azimuthally with respect to each other by 30°, as illustrated by the difference in FIGS. 13b and 13c. Thus, when the sextupole coils 56 and 58 are selectively energized, various desired triangular perturbations may be imposed upon the cross-sectional configuration of the electron beam to substantially cancel or compensate for any sextupole aberrations present in the beam from othe sources.

From the foregoing it may be seen from FIGS. 11a-11e that, by maintaining the current applied to the first quadrupole assembly 52 generally proportional to the sine of twice the angle θ of orientation of the ellipse and maintaining the current applied to the second quadrupole 54 generally proportional to the cosine of twice that angle, the generally elliptical cross-section may be caused to rotate about its center. From these figures it may also be seen that two complete field change cycles are required to produce a 360° rotation of the elliptical focal source. Similarly, by varying currents applied to the sextupole assemblies 56 and 58 in a manner such that the current supplied to the first sextupole coil assembly 56 is generally proportional to the sine of three times the angle θ and the current applied to second sextupole assembly 58 is generally proportional to the cosine of three times that angle θ, the triangular beam cross-section will be caused to rotate about its center, with three complete field change cycles being necessary to produce a 360° rotation of the focal source spacial orientation. Thus, the currents supplied to the various assemblies of the multiple winding assembly 6 are varied as follows, with $I_{Q52}$ and $I_{Q54}$ representing the current flowing through the respective quadrupole coil assemblies 52 and 54 and $I_{S56}$ and $I_{S58}$ representing the current supplied to and flowing through the respective sextupole coil assemblies 56 and 58:

$I_{Q52} = I_{Q0} \sin 2\theta$
$I_{Q54} = I'_{Q0} \cos 2\theta$
$I_{S56} = I_{S0} \sin 3\theta$
$I_{S58} = I'_{S0} \cos 3\theta$ $I_{Q0}$ and $I_{S0}$ represent reference current levels with the primed quantities $I'_{Q0}$ and $I'_{S0}$ taking account of the small differences which are required in the maximum current values for the paired quadrupole assemblies and paired sextupole assemblies, respectively, due mainly to the successively increasing diameter of the overlying multipole windings.

From the foregoing, it is apparent that, in combination with the preliminary focussing coil 4, the multipole winding assembly 6, when energized, will produce different degrees of beam cross-section ellipticity ranging selectively from circular to extremely narrow ellipses and that these cross-sections can be rotated 360° about their own centers and positioned at any given angle by suitable adjustment of the magnitude and polarity of the two quadrupole assembly fields. Similarly, triangular perturbations of the beam cross-section may be deliberately introduced and oriented at any desired angle of rotation around the center of the beam cross-section by adjustment of the magnitude and polarity of the two sextupole assembly fields. Thus, these perturbations can be superimposed upon the focal source in such a manner as to cancel out the sextupole aberrations that may be introduced by the action of the deflecting dipole assemblies 8 and 10 and the other focussing and beam directing elements in the system. These quadrupole and sextupole assemblies comprise principal beam shaping elements for shaping the beam and correcting for such aberrations.

By virtue of the beam shaping elements and beam directing elements described above it becomes possible to select a focal source geometry, i.e., a configuration and orientation of the beam at its impingement with the target 16, which is desirable for high resolution x-ray procedures such as are necessary with computer tomography. For example, a focal source that is a very narrow ellipse that approaches a line source and has its major axis oriented in a plane extending radially outward from the longitudinal axis Z—Z at all azimuthal positions around the large diameter target 16 may be obtained. With this radial line configuration and a suitable choice of the angle of incidence of the beam upon the target, the focal source may have a projected cross-section which appears essentially as a small circular or slightly elliptical source when viewed in the direction of the x-rays. In general, this configuration and orientation permit sharper collimation of the x-ray beam and minimize oblique absorption and penumbral contributions to the total integrated dosage of x-ray applied to the patient or other object of interest.

Figure 4:
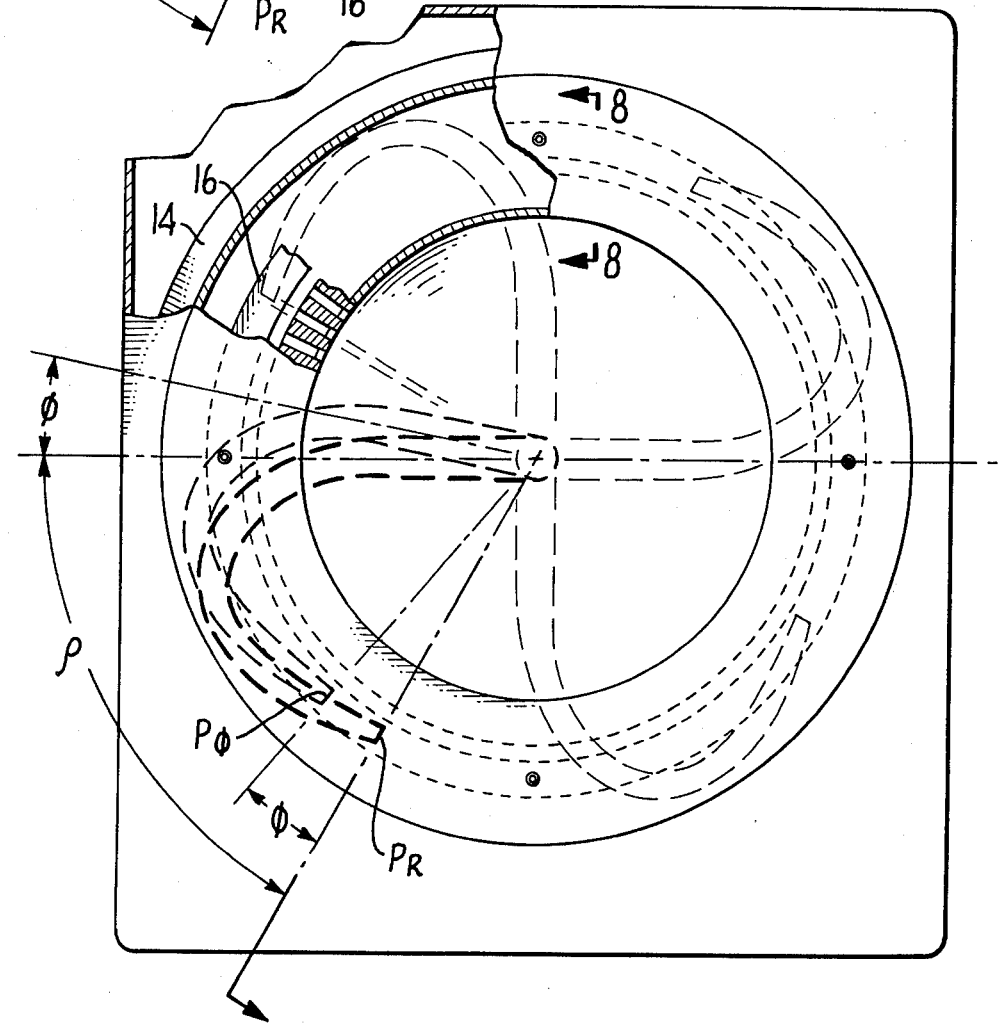
FIG. 4 is a front view, partially in section, of the apparatus of FIG. 1.

From the foreging description of the apparatus and its general manner of operation, the manner in which the beam is directed to the various preselected points upon the target from which x-rays are to be produced to achieve the desired scanning may now be described. For the purpose of this description the reference electron beam will be assumed to be deflected by the dipole assemblies directly along the horizontal dipole reference plane 11 defined above, deflecting the beam directly into the plane of the paper in FIG. 1 and parallel to the surface of the paper in FIG. 2. This reference beam is that indicated by the solid line beam representation of FIG. 3 and the heavy broken line representation of FIG. 4. As illustrated in FIGS. 2–4 the azimuthal component of beam velocity introduced by the fields of large diameter focussing coils 12 and 14 displace the beam angularly about the longitudinal axis Z—Z by an angle $\rho$ measured from the dipole reference plane and thus strikes the target 16 at point $P_r$. Since, for a given electron beam energy, the fields produced by coils 12 and 14 will remain constant and will exert a constant displacing force on the electron beam, the point of impingement of an electron beam under a given condition will always be angularly displaced the same angle $\rho$ from the plane of initial deflection by the dipole assemblies. Also, for purposes of simplifying the description, the apparatus of this preferred embodiment has been configured so that first dipole assembly 8, first quadrupole assembly 52 and first sextupole assembly 56 all have a pole lying in the horizontal dipole reference plane 11, with second dipole 10, second quadrupole 54 and second sextupole 58 each having an antipole in that plane. In the reference situation the beam is deflected initially horizontally by the dipole assemblies to a fixed reference azimuthal and radial position $P_r$ on the annular target 16 by the correct adjustment of focussing coils 12 and 14. This arrangement produces a focal source on the annular target which is essentially a line lying in a radial plane instead of a point source. With this arrangement it is desirable that, at the exit from the dipole deflector assemblies 8 and 10, the beam be slightly convergent in the plane of deflection and divergent in the orthogonal plane. This is achieved by adjusting the current applied to preliminary focussing coil 4 to produce a relatively large diameter, slightly convergent beam at entry to the multipole winding assembly 6 and adjusting the second quadrupole assembly 54 to provide the required convergent/divergent relationship. This adjustment is achieved by applying the proper current from the control (FIG. 2) to the various coils in a manner known to those skilled in the art. For this configuration the preliminary focussing coil 4 focal length is made approximately equal to the distance from that coil 4 to the electron gun 2, and the quadrupole assembly 54 focal length is made similar to the distance from the dipole assemblies to the target 16.

The focussing arrangement is also configured so that, after deflection by the dipole assemblies, a cross-over is produced in the radial plane in the region between the two large diameter opposing field coils 12 and 14. For a given beam energy and current the major and minor axes of the desired elliptical focal source at the annular target can be adjusted by controlling the diameter of the beam at entry to the dipole assemblies and by controlling the strength of the field of the quadrupole 54. However, depending upon the juxtaposition of the fields of the dipole assemblies and the quadrupole 54, even though the center of the focal source is correctly located on the target, the major axis of the generally elliptical beam shape may not be oriented in a desired radial direction at the target. Adjustment of the first quadrupole 52 field now enables the focal source to be rotated about its own center, as described above, and positioned so that its major axis is accurately aligned in a plane extending radially outward from the longitudinal axis Z—Z. The sextupole coil assemblies 56 and 58 may then be adjusted, through the control of the currents applied thereto, to cancel any focal source distortion that may be present due to sextupole aberrations, all by straightforward adjustment of the current supplied to those sextupole assemblies.

Because the coil assemblies 4, 12 and 14 are circularly symmetric about the longitudinal axis Z—Z, this focal source geometry may be maintained for all other azimuthal positions around the target by simply maintaining the following relationship between the dipole, quadrupole and sextupole fields. These relationships are defined for the above described magnetic multipole elements with the respective dipole, guadrupole and sextupole coil currents defined as $I_{D8}$, $I_{D10}$, $I_{Q52}$, $I_{Q54}$, and $I_{S56}$ and $I_{S58}$, respectively. The reference currents, similar to those noted above, are denoted as $I_{D0}$, $I'_{D0}$, $I_{Q0}$, $I'_{Q0}$, $I_{S0}$, and $I'_{S0}$ with the primed figures representing the slight adjustments necessary due to the overlying relationship of the second respective dipole, quadrupole and sextupole assemblies. The relationships thus become:

$I_{D8} = I_{D0} \sin \phi$
$I_{D10} = I'_{D0} \cos (\phi + \epsilon)$
$I_{452} = I_{Q0} \sin (2\phi + \delta)$
$I_{Q54} = I'_{Q0} \cos (2\phi + \delta)$
$I_{S56} = I_{S0} \sin (3\phi + \gamma)$
$I_{S58} = I'_{S0} \cos (3\phi + \gamma)$ In the above equations $\epsilon$ is a constant which makes allowance for non-orthogonality of the dipole, and $\delta$ and $\gamma$ are constants which make allowance for beam rotation due to stray axial fields and for small misalignments of the various multipole coil assemblies.

Since the large diameter focussing coils 12 and 14 rotate the beam by a constant azimuth angle $\rho$, if the dipole deflecting assemblies deflect the beam horizontally, the beam will not strike the target in a horizontal plane but in a plane 60 (FIG. 3) rotated by the angle $\rho$ from the horizontal and thus from the dipole reference plane 11. Thus, the center of this electron beam which is initially deflected horizontally in dipole reference plane 11 strikes the target 16 at azimuthal reference point $P_r$, which lies in the intersection of the target 16 with the rotated plane 60. If the azimuthal position of the beam on the target at any desired point is measured relative to this rotated plane 60, then $\phi$ in the equations above may be considered to be the desired target position angle of the beam upon the target in a coordinate system rotated from the horizontal by the angle $\rho$. The angle $\phi$ in the above equations obviously is also the angle between the plane of deflection 62 of the beam at exit from the dipole assembly and the horizontal plane 11, as illustrated in FIGS. 3 and 4. Thus, the target position angle $\phi$ is defined as the angle about the longitudinal axis Z—Z between the reference point $P_r$ on the target 16 and any desired position $P_\phi$ to which it is desired to direct the electron beam 3 for production of x-rays from that point toward the object of interest lying along the axis Z—Z.

From the equations above it is thus apparent that the current to be applied to the first dipole assembly 8 is generally proportional to the sine of any desired target position angle, and the current applied to the second dipole assembly 10 is generally proportional to the cosine of that desired target position angle. Further, the currents applied to the respective quadrupole coil assemblies 52 and 54 are generally proportional, respectively, to the respective sine and cosine of twice the target position angle, with the current applied to the sextupole assemblies 56 and 58, respectively, being generally proportional to the respective sine and cosine of three times the target position angle.

By suitable variation of these sinusoidal functions the target position angle may be varied with time in any preselected manner to cause the x-rays to be directed at the object of interest from different points on the target in such a preselected sequence. If desired, the target positional angle may be varied by sequential incremental angular steps between successive angularly adjacent locations on the target to effect a generally continuously rotating scan. Alternatively, if desired, the target position angle variation may be made in any other manner, such as in sequential angular steps of slightly more than 180° between successive points on the target 16 so that the application of the appropriate current will cause the x-rays to be directed at the object along the axis from sequential positions on the target with each successive position being almost directly across the longitudinal axis from the immediately preceding position, thus effecting a back and forth scan across the object while rotating it about the target. By suitable control of the target position angle any other scan pattern from uniformly spaced or nonuniformly spaced azimuthal target positions may be effected, including overlapping variable length sectors and, if desired, the use of physiological gating of the beam for triggering the scan.

It may be noted that, in FIG. 1, the electron beam is illustrated as being deflected vertically upward and vertically downward by the dipole assemblies with the extensions of the beam 3 out to the target plane illustrating in side view the displacement of such beams in azimuth by the angle $\rho$. For purposes of illustration only of the manner of impingment of such beams upon the target 16, the extended beams 3' are illustrated as they might appear if "unwrapped", i.e., not displaced in azimuth about the axis Z—Z.

When the conventional, azimuthally rotating scan is desired, progressing from point to point around the annular target 16 at a constant annular speed $\omega$, the dipole assemblies 8 and 10 are excited by drive currents having sinusoidal time dependent amplitudes defined by setting the target position angle $\phi$ equal to $\omega t$, where t is time. By the use of a current stabilized, low distortion, phase coherent harmonic generator for excitation of the multipole windings and assembly 6, the relative radial orientation of the focal source may be held constant as the electron beam rotates around the annular water-cooled target 16.

The x-ray apparatus of this invention may have its beam pulsed onto the target 16 in either of two basic modes. In one arrangement, the electron gun is switched on and off in a succession of preprogrammed pulses while the beam directing elements are being activated to deflect the beam azimuthally about the annular target. In a second, and more preferred arrangement the electron gun may be driven for continuous emission of an electron beam during the full time of the scan with the beam directing elements providing an azimuthal scan by successively deflecting the beam onto and off the target with a preprogrammed azimuthal progression. In the former case the electron beam producing gun 2 which is used preferably is similar to that described in the above referenced article by this inventor, entitled *Recent Advances in High Voltage Electron Beam Injectors*. Such a gun incorporates a biased, nonintercepting extraction electrode which receives positive voltage pulses from a small hot-deck pulser housed in the gun terminal housing. This pulser contains bias and filament supplies and two planar triode switch tubes which are triggered by fiber optic light link 22 from ground potential logic which is designed to pulse the beam on and off rapidly, and to gate the x-ray detectors, over a wide range of pulse repetition frequencies and pulse widths. This arrangement, while providing electron beam pulses in a conventional manner, has a disadvantage in that, to maintain the required electron energy stability during the pulse, either an extremely large capacitor storage bank or a high power electronic voltage regulation system is required. Either requirement adds substantially to the expense, complexity and space requirement for the x-ray apparatus.

With the second mode of operation some of these disadvantageous requirements are avoided. With this second mode of operation, several seconds prior to executing the desired scan of the object of interest, the apparatus is "armed" by switching on a continuously emitting electron beam and directing it into a radiation shielded beam collector 32. The beam collector 32 of FIGS. 1 and 2 is positioned along the longitudinal axis Z—Z just past the dipole assemblies 8 and 10 and facing the electron gun 2. Since considerable energy will be directed into and absorbed by the beam collector 32, a suitable cooling fluid such as water is passed through an internal cavity, such as a series of tubes, within the beam collector to absorb and remove the heat generated by the electron beam impinging thereupon. With the structure illustrated in FIGS. 1 and 2 the electron gun 2 may be energized for producing an electron beam a few seconds before the scan routine is to be executed and with the deflecting dipole assemblies 8 and 10 de-energized. Thus, when production of x-rays is not desired, the beam is never deflected off the longitudinal axis Z—Z but is directed straight through the multipole winding assembly 6 and the dipoles 8 and 10 into the beam collector 32 where the energy is absorbed by the cooling system. This arrangement enables the load on the high voltage power supply, which energizes the electron gun 2, to stabilize prior to the scan routine and then remain constant during the scan procedure when the dipole assemblies are activated. The beam requirements for a high resolution x-ray scanning system indicate the importance of this feature, since the quality of the results depends critically on maintaining a constant electron gun potential during the scan. With a high voltage system an ideal voltage stability of about 0.02% normally is extremely difficult to achieve and maintain when using a pulsed load of relatively high current, as occurs with a high intensity gridded gun x-ray tube. With the beam collector arrangement the necessity for large capacitors or voltage regulating systems is eliminated by loading down the high voltage power supply with a stable DC electron beam which may be absorbed in the collector 32 for several seconds until the switching transients and voltage regulation effects have decayed and a stable equilibrium level of high voltage is attained. After reaching this stability, the azimuthal scan may rapidly be executed by pulsing the deflecting dipole assemblies 8 and 10 and the multipole winding assembly 6 while the electron gun source emission remains constant until completion of the scan, at which time the electron gun 2 is then switched off. For this type of operation, the direct current high voltage system is substantially simplified and the basic voltage uniformity requirement is reduced to satisfying a low ripple specification as can be readily obtained with conventional filter components included in the power supply system.

An alternative arrangement for the beam collector is illustrated in the fragmentary view of FIG. 1a in which a Y is provided in the neck 19 of the vacuum chamber. At the end of the branch 64, which extends off the longitudinally extending neck 19, is provided a beam collector 66, which is generally similar in concept and structure to beam collector 32 of FIG. 1. Selectively operable beam deflecting apparatus is included for selectively either deflecting the electron beam into the collector member 66 or allowing it to continue along the longitudinal axis Z—Z for subsequent production of x-rays at the target. This selectively operable beam deflecting apparatus for deflecting the beam into the collector 66 suitably may comprise a DC biasing electromagnetic dipole assembly 68 mounted onto or adjacent the neck 19 and energized with direct current for providing a continuous biasing force tending to deflect the beam produced by the electron gun 2 off the longitudinal axis and into the collector member 66. Within the neck 19 and on opposite sides of the electron beam emitted by the gun 2 suitably may be placed electrostatic beam deflecting plates 70 which may be selectively energized or de-energized. With this structure, if desired, the beam shaping and directing elements, including the dipole assemblies 8 and 10, may be continuously energized, with the beam deflecting dipole assembly 68 providing an electromagnetic force deflecting the electron beam away from the longitudinal axis and into the beam collector 66 whenever the gun 2 is activated but x-rays are desired not to be produced. Then, when it is desired to initiate the production of x-rays and to initiate the scan routine, the deflecting plates 70 may be energized, preferably with a suitable negative potential, to rapidly inflect the electron beam back to the longitudinal axis Z—Z so that the beam may travel down the neck 19 along that axis for shaping and direction by the various other electromagnetic elements. A generally similar and equivalent structure might dispense with the DC biasing elements 68 and use selective, suitable energization of the deflector plates 70 for selectively either deflecting the beam into the collector 66 or allowing it to continue along the longitudinal axis. This off-axis beam collector arrangement has the desirable feature of removing the beam collector from the position of FIG. 1 in which it is generally adjacent a patient (shown in phantom), being examined by the apparatus.

From the foregoing description it may be seen that this invention provides an electronically scanned X-ray apparatus for producing and nonmechanically scanning high intensity x-rays toward an object of interest from a plurality of different points about that object. While the apparatus and method of this invention has been described with respect to a particularly preferred embodiment, it is to be recognized that numerous modifications and variations of this structure and method, all within the scope of this invention, will readily become apparent to those skilled in the art. Accordingly, the foregoing description of the preferred embodiment is to be considered illustrative only of the principles of the invention and is not to be considered limitative thereof. The scope of this invention is to be limited solely by the claims appended hereto.

What is claimed is:

1. Apparatus for producing x-rays of sufficient intensity for full body tomography and directing such x-rays toward an object of interest from any of a plurality of preselected coplanar points spaced from that object and spaced radially about a line extending through that object, said apparatus having no moving parts and comprising means for producing an electron beam;

stationary target means substantially surrounding a portion of said line and encompassing said coplanar points for receiving said electron beam and producing x-rays from said target points and directing said x-rays toward said object of interest;

an evacuated housing containing said beam producing means adjacent one end and said target means adjacent the opposite end;

means for directing said electron beam selectively to preselected said points on said target means; and beam shaping means for correcting beam aberrations introduced by said beam directing means and for shaping said beam to a predetermined cross-sectional configuration adjacent its point of incidence upon said target, said configuration having a predetermined orientation relative to a line extending radially outwardly from said line through said object to said target point of incidence, and for maintaining said beam configuration and orientation for each said target point of incidence such that the projected beam of x-rays upon said object remains substantially constant from each said target point of incidence, whereby x-rays may be directed toward the object of interest from the target with the combination of the beam directing means and beam shaping means compensating for the effect of space charge forces acting on the beam and correcting for field aberrations imposed thereupon.

2. The apparatus of claim 1 wherein said electron beam producing means and said beam directing means are generally aligned along a longitudinal axis with said electron beam being produced generally along said axis for deflection to said target means.

3. The apparatus of claim 2 wherein said beam directing means comprises two electromagnetic field dipole assemblies having poles oriented orthogonally with respect to one another and with respect to the direction of said electron beam for deflecting said beam outwardly from said axis, said dipole assemblies having poles lying in planes extending radially outwardly of said longitudinal axis at predetermined orientations, with one said radially extending plane being defined as a dipole reference plane and being oriented at a predetermined angle about said axis with respect to an azimuthal reference plane extending radially outwardly of said axis through a point on said target means defined as the azimuthal reference point.

4. The apparatus of claim 3 wherein each said dipole assembly comprises a pair of electromagnetic dipole coils having electric current applied thereto and flowing therethrough to provide the electron beam-deflecting electromagnetic field, said coils being formed around a surface of rotation surrounding said electron beam path and having windings approximately parallel to said beam path and formed such that the current surface density of each portion of each coil is proportional to the cosine of the angle, taken about said longitudinal axis, between said coil portion and an antipole of said dipole coil.

5. The apparatus of claim 4 wherein said current applied to and flowing through the first said dipole assembly is generally proportional to the sine of the desired target position angle, which is defined as the angle about said longitudinal axis between (a) a point on said target means to which it is desired to direct the center of said electron beam, and (b) said azimuthal reference point, and wherein said current applied to and flowing through the second said dipole assembly is generally proportional to the cosine of said desired target position angle.

6. The apparatus of claim 5 wherein said target position angle varies with time in a preselected manner, whereby application of said current to the dipole assemblies may cause the x-rays to be directed at the object from different points on the target in a preselected sequence.

7. The apparatus of claim 6 wherein said target position angle variation comprises sequential incremental angular steps between successive angularly adjacent locations on said target means about said object, whereby application of said current to the dipole assembly may cause the x-rays to be directed at the object sequentially from those angularly adjacent locations.

8. The apparatus of claim 6 wherein said target position angle variation comprises sequential angular steps of slightly more than 180 degrees between successive said points on said target means, whereby application of said current to the dipole assembly may cause the x-rays to be directed at the object from sequential positions on the target with each successive position being almost directly across said longitudinal axis from the immediately preceding said position.

9. The apparatus of claim 3 wherein said beam directing means further comprises means for controlling electron beam spreading due to space charge forces.

10. The apparatus of claim 9 wherein said beam spreading controlling means comprises electromagnetic focussing means defined by at least one coil having a current passing therethrough, said focussing means surrounding a portion of said electron beam path and positioned axially between said dipole assemblies and said target to provide an electromagnetic field through which said electron beam path passes.

11. The apparatus of claim 10 wherein said focusing means electromagnetic field is of a predetermined strength and distribution to substantially cancel at said target plane any radial component of the velocity of said electron beam passing therethrough.

12. The apparatus of claim 10 wherein said electromagnetic focussing means comprises two said coils spaced apart from one another along said longitudinal axis with the first said coil axially proximal said dipole assemblies and the second said coil axially proximal said target.

13. The apparatus of claim 12 wherein the first said coil has a current of a predetermined polarity and a first predetermined magnitude passing therethrough and the second said coil has a current of the opposite polarity and a second predetermined magnitude passing therethrough, such that the combined net axial field components of said coils are reduced to zero adjacent said target, whereby the azimuthal beam velocity components introduced by each of the two electrically energized coils on the electron beam substantially cancel one another and the net azimuthal velocity of the electron beam is reduced substantially to zero as the beam strikes the target.

14. The apparatus of claim 13 wherein said second current magnitude is substantially equal to said first current magnitude, whereby a single, constant current power supply may be used for both lenses.

15. The apparatus of claim 3 wherein said beam shaping means comprises an electromagnetic preliminary focussing element defined by at least one coil having a current passing therethrough, said preliminary focussing element surrounding a portion of said electron beam path and positioned axially between said electron beam producing means and said dipole assemblies.

16. The apparatus of claim 3 wherein said beam shaping means comprises means for shaping said electron beam into a generally elliptical cross-section at its point of incidence upon said target, with the major axis of said generally elliptical figure lying generally in a plane extending radially outwardly of said longitudinal axis.

17. The apparatus of claim 16 wherein said elliptical shaping means comprises at least one electromagnetic quadrupole assembly formed around said electron beam path between said electron beam producing means and said dipole assemblies to provide an electron beam-shaping electromagnetic field.

18. The apparatus of claim 17 wherein said quadrupole assembly comprises four electromagnetic coils having electrical current applied thereto and flowing therethrough to provide said electron beam-shaping electromagnetic field, said coils being formed about a surface of rotation surrounding said beam path, said coils each having windings extending approximately parallel to said beam path and subtending sequentially adjacent arcs of approximately 90 degrees about said surface of rotation, said coil windings being formed such that the current surface density of each portion of each said coil is proportional to the cosine of the angle between said coil portion and an antipole of said quadrupole coil.

19. The apparatus of claim 17 wherein said elliptical shaping means comprises two said electromagnetic quadrupole assemblies, the first said quadrupole assembly being oriented about said longitudinal axis such that one pole of said first quadrupole assembly lies generally in said dipole reference plane, and the second said quadrupole assembly being concentric with the first said quadrupole assembly and being angularly displaced 45° about said longitudinal axis with respect to said first quadrupole assembly.

20. The apparatus of claim 19 wherein said current applied to and flowing through said first quadrupole assembly is generally proportional to the sine of twice the desired target position, which is defined as the angle about said longitudinal axis between (a) a point on said target means to which it is desired to direct the center of said electron beam and (b) said azimuthal reference point, and wherein said current applied to and flowing through said second quadrupole assembly is generally proportional to the cosine of twice said desired target position angle.

21. The apparatus of claim 3 wherein said beam shaping means comprises means for correcting sextupole aberrations introduced into said electron beam by other beam directing and shaping elements of the apparatus.

22. The apparatus of claim 21 wherein said sextupole aberration correcting means comprises at least one electromagnetic sextupole coil assembly formed around said electron beam path between said electron beam producing means and said dipole assemblies to provide an electromagnetic field for controlling and introducing preselected triangular perturbations into the cross-sectional configuration of said electron beam to substantially cancel any sextupole aberrations present in said electron beam.

23. The apparatus of claim 22 wherein each said sextupole coil assembly comprises six electromagnetic coils having electrical current applied thereto and flowing therethrough to provide said perturbation controlling and introducing field, said coils being formed about a surface of rotation surrounding said beam path, said coils each having windings extending approximately parallel to said beam path and subtending sequentially adjacent arcs of approximately 60° about said surface of rotation, with said coil windings being formed such that the current surface density of each portion of each said coil is generally proportional to the cosine of the angle between said coil portion and an antipole of said sextupole coil.

24. The apparatus of claim 23 wherein said sextupole aberration correcting means comprises two said sextupole coil assemblies, the first said sextupole coil assembly being oriented about said longitudinal axis such that one pole of said first sextupole assembly lies generally in said dipole reference plane, and the second said sextupole coil assembly being concentric with the first said sextupole coil assembly and being angularly displaced 30° about said longitudinal axis with respect to said first sextupole coil assembly.

25. The apparatus of claim 24 wherein said current applied to and flowing through said first sextupole coil assembly is generally proportional to the sine of three times the desired target position angle, which is defined as the angle about said longitudinal axis between (a) a point on said target means to which it is desired to direct the center of said electron beam and (b) said azimuthal reference point, and wherein said current applied to and flowing through said second sextupole assembly is generally proportional to the cosine of three times said desired target position angle.

26. The apparatus of claim 2 further comprising x-ray shielded beam collector means for receiving said electron beam whenever said electron beam is not directed to said target.

27. The apparatus of claim 26 wherein said beam collector means comprises a member having an internal cavity connected to an inlet and an outlet for passage of a cooling fluid therethrough.

28. The apparatus of claim 26 further comprising means for selectively directing said beam away from said beam collector means to said target, whereby an electron beam may be produced and received into said beam collector and then, after a desired period of time suitable for stabilizing the electron beam voltage, may be directed to any selected portion of the target to produce a generally stabilized output level of x-rays for a predetermined duration until the beam is permitted to return to the beam collector means.

29. The apparatus of claim 26 wherein said beam collector means comprises a collector member positioned on said longitudinal axis distal said beam producing means, whereby the beam may be received into the beam collector whenever the beam producing means is activated and the beam directing means is not activated to deflect the beam off that axis to the target.

30. The apparatus of claim 26 wherein said beam collector means comprises a collector member displaced from said longitudinal axis and selectively operable beam collector beam deflecting means for selectively either deflecting said electron beam from said longitudinal axis to said collector member or allowing said electron beam to continue along said longitudinal axis past said collector member, whereby the beam may be allowed to pass along the longitudinal axis past the collector when x-rays are desired to be produced from the target but may be deflected into the collector member when x-rays are not to be produced from the target while the beam producing means is activated.

31. The apparatus of claim 2 wherein said electron beam producing means includes means for pulsing said electron beam on and off for predetermined periods of time while said beam directing means is being activated to direct said electron beam to preselected points on said target, whereby electron beam pulses of predetermined duration may be directed to the preselected points on the target for production of pulses of x-rays thereat.

32. The apparatus of claim 1 wherein said target means comprises an annular structure spaced from said object of interest in a generally radial direction.

33. The apparatus of claim 32 wherein said annular target comprises at least one member having an interior chamber connected to an inlet and an outlet for passage of a cooling fluid therethrough.

34. The apparatus of claim 32 wherein said evacuated housing includes, at the end adjacent said target, a cavity open at its outer end and extending inwardly of said housing and being defined by wall means extending about said axis from said housing end, past said target plane and part-way to said electron beam producing means, whereby the object of interest may be inserted into the cavity for reception of the x-rays from the target.

35. The apparatus of claim 34 further comprising x-ray window means mounted to said housing and positioned between said target and said cavity for permitting passage therethrough of said x-rays from said target to said object of interest.

36. The apparatus of claim 35 further comprising means positioned between said target and said object of interest for collimating said x-rays along a predetermined path.

37. The apparatus of claim 36 wherein said collimating means comprises a plurality of elements spaced apart around the periphery of said cavity-defining wall member.

38. The apparatus of claim 37 wherein said collimating means are configured to direct said x-ray beam substantially radially inward of said target.

39. The apparatus of claim 38 further comprising a plurality of x-ray detectors mounted adjacent said cavity-defining wall member and angularly positioned between adjacent said collimating means elements.

40. The apparatus of claim 37 wherein said collimating means are configured to direct said x-ray beam slightly longitudinally outwardly of said cavity.

41. The apparatus of claim 40 further comprising a plurality of x-ray detectors mounted across said axis from and aligned with said collimating means.

42. A method of producing x-rays of sufficient intensity for full body tomography and directing said x-rays toward an object of interest from a fixed, annular target spaced radially from a line extending through that object, comprising the steps of producing an electron beam directed toward said object of interest along a longitudinal axis generally parallel with said line through said object, selectively directing said beam, by means of selectively activated electromagnetic elements having no mechanically moving elements, to preselected points on said fixed, annular target for production of x-rays from said points to said object, and correcting selected beam aberrations imposed upon said beam by said beam-directing elements, and shaping said beam to a predetermined cross-sectional configuration at its point of incidence on said target, said configuration having a predetermined orientation relative to a line extending radially outwardly from said line through said object to said target point of incidence, and for maintaining said beam configuration and orientation for each said target point of incidence such that the projected beam of x-rays upon said object remain substantially constant from each said target point of incidence.

43. The method of claim 42 wherein said beam directing comprises applying a radially outward velocity component to said electron beam by an electromagnetic beam directing element to deflect said beam away from said longitudinal axis for direction toward said annular target.

44. The method of claim 43 wherein said beam directing further comprises focussing said beam onto said target by applying an electromagnetic focussing force thereto to compensate for beam spreading effects of space charges in said beam.

45. The method of claim 44 wherein said beam directing and focussing further comprises substantially neutralizing said radially outward beam velocity component a predetermined radial distance outward of said longitudinal axis.

46. The method of claim 45 wherein said focussing force is applied by electrically energizing at least one circumferentially extending coil located radially outward of said deflected electron beam.

47. The method of claim 45 further comprising substantially neutralizing any azimuthal beam velocity components directed circumferentially about said longitudinal axis prior to said beam reaching said target, whereby the electron beam strikes the annular target with substantially no azimuthal velocity.

48. The method of claim 47 wherein said azimuthal beam velocity components are neutralized by application of an electromagnetic field of predetermined magnitude and direction to said electron beam.

49. The method of claim 48 wherein said azimuthal beam velocity-neutralizing field is applied to said electron beam by electrically energizing with currents of predetermined magnitude and polarity two circumferentially extending coils spaced apart along said longitudinal axis and located radially outward of said deflected electron beam.

50. The method of claim 42 wherein said beam cross-sectional configuration is generally circular.

51. The method of claim 42 wherein said beam cross-sectional configuration is generally elliptical.

52. The method of claim 51 wherein said generally elliptical cross-section has its major axis lying generally in a plane extending radially outwardly of said longitudinal axis.

53. The method of claim 52 wherein said beam is directed slightly radially inwardly at its point of incidence upon said target, and wherein said annular target is angled radially inwardly such that the projected image of said x-rays onto said object of interest is substantially circular in cross section.

54. The method of claim 53 wherein said x-rays are projected along a path extending radially inwardly of said beam point of incidence upon said target.

55. The method of claim 54 wherein said x-rays are collimated along said path, whereby the x-rays may be directed at a preselected point on the object of interest.

56. The method of claim 53 wherein said x-rays are projected along a path toward an x-ray detector which is positioned across said longitudinal axis from and slightly longitudinally outward of said beam point of incidence upon said target.

57. The method of claim 56 wherein said x-rays are collimated along said path.

58. The method of claim 42 wherein said beam aberrations are corrected by passing said electron beam through adjustable quadrupole and sextupole electromagnetic fields, whereby the interaction of the quadrupole and sextupole fields may serve to correct for higher order aberrations introduced into the beam by its deflection and direction to the target by the beam directing elements.

59. The method of claim 42 wherein said electron beam is received into an x-ray shielded beam collector when said electron beam is being produced while x-rays are not desired to be produced from said target, whereby the electron beam may be produced and stabilized with the energy from the electron beam being absorbed and dissipated in the beam collector.

60. The method of claim 59 wherein said beam collector is positioned on said longitudinal axis facing said electron beam and receives said electron beam when said selective beam directing elements are not activated, but from which said electron beam is deflected when said selective beam directing elements are activated.

61. The method of claim 60 wherein said beam directing elements are activated intermittently at preselected intervals for preselected periods, whereby the electron beam impinges upon the target in pulses to produce intermittent pulses of x-rays of predetermined duration at predetermined intervals therefrom.

62. The method of claim 60 wherein said electron beam is received into said beam collector when said beam is initially produced, and then, when the voltage of said beam has stabilized, said beam directing elements are activated to direct said beam to said target for the production of x-rays, whereby a generally stabilized output level of x-rays is produced from the target.

63. The method of claim 59 wherein said electron beam is selectively directed at preselected times off said longitudinal axis and into said beam collector prior to reaching said target and at other times along said longitudinal axis for subsequent deflection to said target, whereby the selected deflection off the longitudinal axis enables the beam directing elements to remain activated during periods when the electron beam is being produced but x-rays are not desired to be produced from the target.

64. The method of claim 62 wherein said electron beam is deflected into said beam collector prior to its reaching said selective beam directing elements.

65. The method of claim 42 wherein said electron beam is produced in intermittent pulses of predetermined duration, whereby pulses of x-rays of predetermined duration may be produced from the preselected target points by the impingement of the electron beam pulses thereupon.

* * * * *

UNITED STATES PATENT OFFICE
CERTIFICATE OF CORRECTION

Patent No. 4,130,759　　　　　　　　　　Dated December 19, 1978

Inventor(s) Jacob Haimson

It is certified that error appears in the above-identified patent and that said Letters Patent are hereby corrected as shown below:

column 2, line 34 correct the equation to read:

$$z = (r_o/\sqrt{i}) \, (\gamma^2-1)^{3/4} \, G \text{ in MKS units.}$$

Column 4, line 32 change "taret" to --target--.

IN THE DRAWING:

UNITED STATES PATENT OFFICE   Page 2 of 2
CERTIFICATE OF CORRECTION

Patent No. 4,130,759              Dated December 19, 1978

Inventor(s) Jacob Haimson

It is certified that error appears in the above-identified patent and that said Letters Patent are hereby corrected as shown below:

In Figure 3 delete the reference numeral "64";

Correct Figure 5 to appear as shown below.

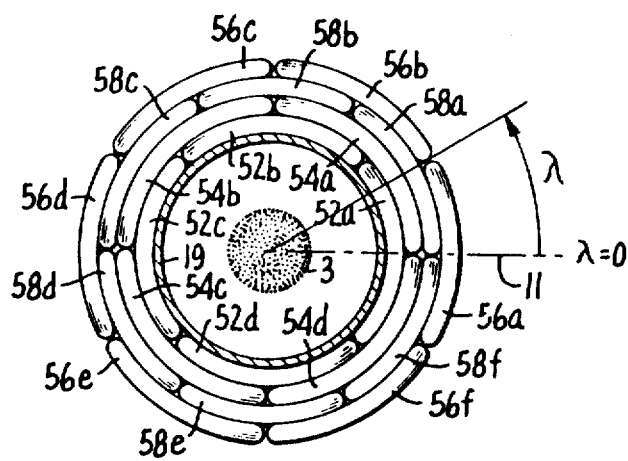

FIG. 5.

Signed and Sealed this

Twentieth Day of March 1979

[SEAL]

Attest:

RUTH C. MASON
Attesting Officer

DONALD W. BANNER
Commissioner of Patents and Trademarks